(12) United States Patent
Zjawiony et al.

(10) Patent No.: US 7,687,538 B2
(45) Date of Patent: Mar. 30, 2010

(54) AGENTS WITH SELECTIVE κ-OPIOID RECEPTOR AFFINITY

(75) Inventors: Jordan Zjawiony, Oxford, MS (US); Hesham Fahmy, Brookings, SD (US); David Jeremy Stewart, Brevard, NC (US); Bryan Roth, Moreland Hills, OH (US)

(73) Assignees: University of Mississippi, University, MS (US); Case Western Reserve University, Cleveland, OH (US)

( * ) Notice: Subject to any disclaimer, the term of this patent is extended or adjusted under 35 U.S.C. 154(b) by 623 days.

(21) Appl. No.: 11/192,925

(22) Filed: Jul. 29, 2005

(65) Prior Publication Data

US 2006/0083679 A1    Apr. 20, 2006

Related U.S. Application Data

(60) Provisional application No. 60/592,996, filed on Jul. 30, 2004.

(51) Int. Cl.
*A61K 31/35* (2006.01)
*C07D 493/00* (2006.01)

(52) U.S. Cl. .................................. 514/455; 549/280
(58) Field of Classification Search ................ 549/280; 514/455
See application file for complete search history.

(56) References Cited

OTHER PUBLICATIONS

Chavkin et al, Jol. Pharm. & Exp. Thera. vol. 308 No. 3 pp. 1197-1203 (2004).*
Stewart et al., Arzneim-Forsch/Drug Res.; 56:4; 2006; pp. 269-275.
Koreeda et al., Chem. Abs.; vol. 114; No. 62406; 1990; best available.
Giroud et al., Forensic Science International; vol. 112; 2000; pp. 143-150.
Valdes et al., Organic Letters; vol. 3; No. 24; 2001; pp. 3935-3937.
Boultais, et al.; New chemo-enzymatic synthesis of very high specific radioactivity [35S] (S) methionine [1]. *J. Label. Cmpds. Radiopharm.* 1997, 39, 621-624.
Butelman, et al.; The plant-derived hallucinogen, salvinorin A produces O-opioid agonist-like discriminative effects in rhesus monkeys. *Psychopharm* 2004, 172, 220-224.
Capasso, et al.; The hallucinogen her *Salvia divinorum* and its active ingredient Salvinorin A inhibit enteric cholinergic transmission in the guinea-pig ileum.
Chavkin, et al.; Salvinorin A is a Highly Efficacious Kappa Opioid Receptor Agonist, *JPET*, 2004, 308, 1197-1203.
Chao, et al.; Kappa-opioid potentiation of tumor necrosis factor-alpha-induced anti-HIV-1 activity in acutely infected human brain cell cultures. *Biochem. Pharmacol.* 1998, 56, 397-404.
Egli, et al.; Synthesis of labeled captopril. *J. Label. Cmpds. Radiopharm.* 1987, 25, 1105-1115.
McCurdy, et al.; Studies directed toward understanding the opioid receptor recognition of Salvinorin A, a non-nitrogenous natural product with kappa opioid receptor selectivity; INRC; Jul. 6-11, 2003.
Ortega, et al.; Salvinorin, a new trans-neoclerodane diterpene from *Salvia divinorum* (Labiatae), *J. Chem. Soc., Perkin Trans.* 1, 1982, 10, 2505-2508.
Roth, et al.; Salvinorin A : A potent, naturally occurring, non-nitrogenous O-opioid selective agonist, *PNAS*, 2002, 99(10), 11934-11939.
Siebert, D.J., *Salvia divinorum* and Salvinorin A: New pharmacological findings. *J. Ethnopharmacol.* 1994, 43, 53-56.
Valdes III, et al.; Divinorin A, a psychotropic terpenoid, and Divinorin B from the hallucinogenic Mexican mint *Salvia divinorum*. *J. Org. Chem.* 1984, 49, 4716-4720.
Yan, et al.; Identification of the molecular mechanisms by which the Diterpenoid Salvinorin A Binds to k-Opioid Receptors; Biochemistry; 2005; 44; pp. 8643-8651.

* cited by examiner

*Primary Examiner*—Janet L. Andres
*Assistant Examiner*—Raymond Covington
(74) *Attorney, Agent, or Firm*—Stites & Harbison PLLC; Richard S. Myers, Jr.

(57) ABSTRACT

Compounds and compositions that are salvinorin A and salvinorin B derivatives that demonstrate selectivity and/or potency for the k-opioid receptor (KOR), allowing for their use as medicines, as well as chemical probes (both radiolabeled and cold) for fields utilizing the techniques of radiolabeled binding assays.

21 Claims, No Drawings

AGENTS WITH SELECTIVE κ-OPIOID RECEPTOR AFFINITY

PRIORITY INFORMATION

This application claims benefit to U.S. Patent Application No. 60/592,996, filed Jul. 30, 2004, the contents of which are incorporated herein by reference.

GOVERNMENT SUPPORT

This invention is a result of research made with support from the National Institutes of Health Grant Number 5 RO1 DA-017229-04-02. The United States Government has certain rights to this invention.

FIELD OF THE INVENTION

The present invention relates to the field of salvinorin A and salvinorin B derivatives, and κ-opioid receptor (KOR) activating agents.

BACKGROUND OF THE INVENTION

Salvinorin A is a hallucinogenic neoclerodane diterpene isolated from the leaves of *Salvia divinorum* (Ortega 1982, Valdez 1984). Receptor binding studies revealed salvinorin A as a full agonist that has remarkable affinity as well as selectivity for the kappa opiate receptor (KOR) (Roth 2002). Salvinorin A is the most potent natural psychedelic agent thus far reported with a human dose ranging between 0.5-1 mg (Siebert 1994). This is the first reported example of an hallucinogen acting through the opiate receptor system and the first non-nitrogenous ligand that binds with high affinity/selectivity to a G protein-coupled receptor.

The KOR has been implicated in a wide variety of disease processes including: dementia, mood disorders, depression, schizophrenia, drug abuse, alcohol addiction, chronic pain conditions, seizure disorders, cognition enhancement, congestive heart failure, renal failure, augmentation of renal function, and diuresis. Thus, long-acting agonists or antagonists are very useful for a variety of disease states, and very useful for pharmacological studies of KOR activity. In particular, Salvinorin A-derived agonists which do not cross the blood brain barrier would be ideal to treat peripheral chronic pain conditions (osteo- and rheumatoid arthritis, degenerative joint disease, sciatica, and so on), congestive heart failure, renal failure, augmentation of renal function and diuresis, cancer, and HIV (Chao et al. 1998), while salvinorin A derived antagonists which cross the blood-brain barrier would be useful for treating mood disorders, schizophrenia, dementia, drug abuse, alcohol addiction, chronic central pain conditions, seizure disorders, HIV-related neuropsychiatric disorders, brain and spinal cord tumors and cognition enhancement.

The KOR system is a pharmaceutical curiosity due to its ability to modulate pain without causing euphoria, and hence addiction, through stimulation. In a recent report, it was shown that salvinorin A activates KOR's in subhuman primates and that the actions of salvinorin A are similar to those of other KOR agonists in vivo (Butleman et al. 2004). The hallucinogenic activity of salvinorin A also suggests the KOR plays some role in perception. Semi-synthetic modifications to the salvinorin skeleton may yield non-addictive opioid analgesics and/or KOR selective agonists or antagonists to treat the wide array of diseases associated with KOR.

SUMMARY OF THE INVENTION

As stated herein, one aspect of the present invention is compounds of the following formula:

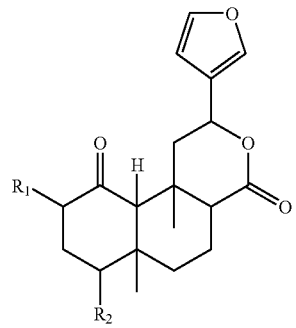

wherein the variables are defined below. Also included are derivatives and salts thereof. The compounds of the present invention can be isotopically labeled and/or can be part of a pharmaceutical composition.

Isotopically labeled compounds of the present invention can be used in methods of diagnostic screening such as, for example, those using PET, SPECT, and NMR spectroscopy. These compounds can be used in receptor-binding assays. Receptor-binding assays provide critical information in drug lead identification and later lead characterization processes. They are one of the most commonly used techniques to characterize the structure and activity of receptor proteins. The receptor-binding assay is designed as a competitive inhibition assay using the radiolabeled known drug/ligand receptor interaction to screen chemical or natural product libraries for more effective biologically active compounds. These quantitative binding parameter determinations indicate the minimal effective drug concentrations, as well as the selectivity of the ligand for the receptor.

Thus, the imaging aspects of the present invention are useful in the fields of molecular biology and pharmacology as radioligands for radio-receptor binding assays for drug discovery, diagnostic and research-related applications and for in vitro and in vivo imaging studies. These aspects of the present invention include methods for diagnostic studies for a variety of illnesses, and for diagnostic and prognostic studies of KOR-expressing tumors and for following the course of chemotherapy on KOR-expressing tumors.

DESCRIPTION OF THE INVENTION

In the search for new KOR activating agents, the natural neoclerodane diterpene, salvinorin A, is chemically modified to yield stable, yet reactive intermediates allowing for a wide variety of structural diversifications. The derivatives of the present invention show selectivity and/or potency for the KOR, allowing for their use as medicines, as well as chemical probes (both radiolabeled and cold) for fields utilizing the techniques of radiolabeled binding assays.

One aspect of the present invention is a compound of the following general formula, including derivatives and salts thereof:

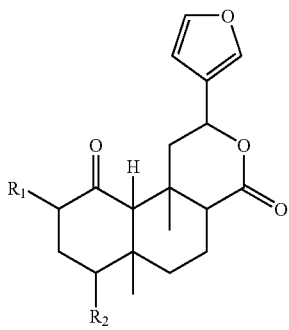

wherein:

R$_1$ and/or R$_2$ is hydrogen, halogen, alkyl, hydroxyl, alkoxyl, acyloxyl, hydroxyalkyl, amino, alkylamino, acylamino, acetylalkylamino, arylamino, arylalkylamino, Het-alkylamino, aminoalkyl, acylaminoalkyl, nitroalkyl, thiol, alkylthio, acylthio, arylthio, arylalkylthio, acetylalkylthio, carboxylic and derivatives thereof (such as esters, amides, and nitriles).

These and all other compounds of the present invention may comprise at least one isotopic label. For example, in embodiments of the present invention, radioisotopes of hydrogen, carbon, oxygen, sulfur- and nitrogen atoms may be present on the R$_1$ and/or R$_2$ substituents when the compounds of the present invention are used in experiments utilizing radiolabeled ligands.

Another aspect of the present invention is a compound of the following general formula, and analogs and salts thereof:

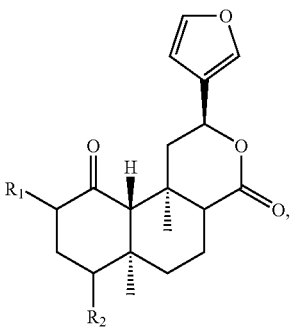

wherein R$_1$ and R$_2$ are defined above. These compounds may be isotopically labeled.

As used herein, the term alkyl or alkyl group is to be understood in the broadest sense to mean hydrocarbon residues which can be linear, i.e., straight-chain, or branched, and can be acyclic or cyclic residues or comprise any combination of acyclic and cyclic subunits. Further, the term alkyl as used herein expressly includes saturated groups as well as unsaturated groups which latter groups contain one or more, for example, one, two, or three, double bonds and/or triple bonds.

All these statements also apply if an alkyl group carries substituents or occurs as a substituent on another residue, for example, in an alkyloxy residue, or an arylalkylamino residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl (=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like (C$_2$-C$_6$)-alkenyl and (C$_2$-C$_6$)-alkynyl, and cyclic alkyl groups containing from 3 to 8 ring carbon atoms, in particular from 3 to 6 ring carbon atoms. A particular group of saturated acyclic alkyl residues is formed by (C$_1$-C$_4$)-alkyl residues like methyl, ethyl, n-propyl, isopropyl, n-butyl, isobutyl, sec-butyl, and tert-butyl.

The alkyl groups of the present invention can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen atoms (i.e., haloalkyl, hydroxyl).

Examples of substituted cycloalkyl groups are cycloalkyl groups which carry as substituent one or more, for example, one, two, three, or four, identical or different acyclic alkyl groups, for example, acyclic (C$_1$-C$_4$)-alkyl groups like methyl groups. Examples of substituted cycloalkyl groups are 4-methylcyclohexyl, 4-tert-butylcyclohexyl, or 2,3-dimethylcyclopentyl.

As used herein, the term "amino" means —NH$_2$; the term "nitro" means —NO$_2$; the term "halogen" designates —F, —Cl, —Br or —I; the term "thiol" means —SH; the term "hydroxyl" means —OH; the term "sulfonyl" means —SO$_2$—.

The term "thio" refers to a group having a —S— attached thereto, such as "alkylthio" (—S-alkyl).

The term aryl refers to a monocyclic or polycyclic hydrocarbon residue in which at least one carbocyclic ring is present. In a (C$_6$-C$_{14}$)-aryl residue from 6 to 14 ring carbon atoms are present. Examples of (C$_6$-C$_{14}$)-aryl residues are phenyl, naphthyl, biphenylyl, fluorenyl, or anthracenyl. Examples of (C$_6$-C$_{10}$)-aryl residues are phenyl or naphthyl. Unless stated otherwise, and irrespective of any specific substituents bonded to aryl groups, aryl residues including, for example, phenyl, naphthyl, and fluorenyl, can in general be unsubstituted or substituted by one or more, for example, one, two, three, or four, identical or different substituents. Aryl residues can be bonded via any desired position, and in substituted aryl residues the substituents can be located in any desired position.

The "Het" group comprises groups containing 3, 4, 5, 6, 7, 8, 9, or 10 ring atoms in the parent monocyclic or bicyclic heterocyclic ring system. In monocyclic Het groups, the heterocyclic ring preferably is a 3-membered, 4-membered, 5-membered, 6-membered, or 7-membered ring, particularly preferably, a 5-membered or 6-membered ring.

Alkoxy as used herein means an alkyl-O— group in which the alkyl group is as previously described. Exemplary alkoxy groups include methoxy, methoxy methyl, ethoxy, n-propoxy, i-propoxy, n-butoxy, t-butoxy and polyethers including —O—$(CH_2)_2$ $OCH_3$.

An acyl group is defined as a group —C(O)R where R is an alkyl or aryl radical and includes acetyl, trifluoroacetyl, benzoyl and the like.

Where terms are used in combination, the definition for each individual part of the combination applies unless defined otherwise. For instance, arylalkylthio refers to an aryl group, as defined above, alkyl group as defined above, and a thio group. An example is alkylamino, which is defined as a nitrogen atom substituted with an alkyl of 1 to 12 carbon atoms. Also, thioalkyl, or alkylthio as used herein means an alkyl-S— group in which the alkyl group is as previously described. Thioalkyl groups include thiomethyl and the like. Examples of alkylthio groups of compounds of the present invention includes those groups having one or more thioether linkages and from 1 to about 12 carbon atoms, further examples have from 1 to about 8 carbon atoms, and still further examples have 1 to about 6 carbon atoms. Alkylthio groups having 1, 2, 3 or 4 carbon atoms are further examples.

Some of the compounds of the invention may have stereogenic centers. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. Thus, when using the term compound, it is understood that all stereoisomers are included.

Another aspect of the present invention is methods of use for the compounds of the present invention.

For therapeutic use, the compounds of the present invention may be in the form of a composition that comprises one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The compounds of the present invention may additionally be obtained or used as inorganic or organic salts using methods known to those skilled in the art. It is well known to one skilled in the art that an appropriate salt form is chosen based on physical and chemical stability, flowability, hydroscopicity and solubility. Pharmaceutically acceptable salts of the present invention with an acidic moiety may be optionally formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be optionally formed from organic and inorganic acids.

For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo. When using the term compound herein, it is understood that all salts are included.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

For diagnostic use, aspects of the invention include the compounds disclosed herein further including an isotopic label, and pharmaceutical compositions containing the labeled compounds, which are useful in methods of diagnosing disease and/or methods of monitoring the progression of a disease state. These methods include the steps of administering to a mammal a detectable labeled compound of the present invention, and detecting the binding of that compound to the KOR. These compounds and compositions are useful in SPECT (single photon emission computed tomography), and PET (positron emission tomography), and NMR imaging.

When used as chemical probes, the compounds of the present invention can be used as disclosed in WO 2004/052889, incorporated herein by reference.

The present invention is useful in the diagnosis of a wide variety of diseases and disorders including any one or more or a combination of the following: dementia, mood disorders, depression, schizophrenia, drug abuse, alcohol addiction, chronic pain conditions, seizure disorders, cognition enhancement, congestive heart failure, renal failure, augmentation of renal function, and diuresis.

The invention includes isotopically-labeled compounds, wherein at least one atom of compounds of the present invention is an atom having an atomic mass or mass number different from the atomic mass or mass number most abundantly found in nature. Examples of isotopes that can be incorporated into compounds of the invention include isotopes of hydrogen, carbon, nitrogen, oxygen, phosphorous, fluorine, sulfur, iodine, and chlorine, such as $^2H$, $^3H$, $^{11}C$, $^{13}C$, $^{14}C$, $^{13}N$, $^{15}N$, $^{15}O$, $^{37}O$, $^{35}S$, $^{18}F$, $^{19}F$, $^{99m}Tc$, $^{123}I$, and $^{125}I$. Compounds of the present invention and pharmaceutically acceptable salts and prodrugs of said compounds that contain the aforementioned isotopes and/or other isotopes of other atoms are within the scope of the invention. Isotopically-labeled compounds of the present invention are useful in drug and/or substrate tissue distribution and target occupancy assays. For example, as stated above, these compounds are particularly useful in SPECT, PET, and NMR.

SPECT acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Examples of viable SPECT isotopes include, but are not limited to, 123-iodine ($^{123}I$) and 99m-technetium ($^{99m}Tc$). A mammal is injected with a radioactively labeled agent at tracer doses. Tracer doses are doses sufficient to allow the diagnosis to occur (e.g., to allow detection of the labeled compound) but are not sufficient to have a therapeutic effect on the mammal. The nuclear decay resulting in the emission of a single gamma ray which passes through the tissue and is measured externally with a SPECT camera. The uptake of radioactivity reconstructed by computers as a tomogram shows tissue distribution in cross-sectional images.

PET is a technique for measuring the concentrations of positron-emitting isotopes within the tissues. Like SPECT, these measurements are, typically, made using PET cameras outside of the living mammals. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography, published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long-term radiation exposure that a mammal receives from high dosages required during PET imaging.

In certain instances, PET imaging can be used to measure the binding kinetics of compounds of this invention with KOR. For example, administering an isotopically labeled compound of the invention that penetrates into the body and binds to a KOR creates a baseline PET signal which can be monitored while administering a second, different, non-isotopically labeled compound. The baseline PET signal will decrease as the non-isotopically labeled compound competes for the binding to the KOR.

The compounds of the present invention may be administered by any suitable route, preferably in the form of a pharmaceutical composition adapted to such a route, and in a dose effective to image and desirably quantify KOR activity in the brain. Preferably, the compounds are administered intravenously to minimize metabolism before the compound enters the brain. The amount of the compounds of the present invention required to image or quantify KOR activity in the brain will be readily ascertained by one of ordinary skill in the nuclear medicine art taking into account the specific activity of the compound and the radiation dosimetry. As is known by those skilled in the nuclear medicine art, the number of milliCuries of the radiolabeled compounds to be administered for the PET or SPECT scan will be limited by the dosimetry, whereas the mass of compound to be administered (e.g., μg/kg or mg/kg of body weight of the patient) is calculated based on the specific activity of the synthesized compound, i.e., the amount of radioactivity/mass, of radiolabeled compound. It will be appreciated that because of the short half-life of the radioisotopes, e.g., about 2 hours for $^{18}F$ and about 20 minutes for $^{11}C$, it is often necessary to make the radiolabeled compound at or near the site of administration. For $^{123}I$, the half-life is slightly longer, being about 13 hours. The specific activity of the compounds must then be ascertained in order to calculate the proper dosing. Such techniques are well known to those skilled in the art.

Salvinorin A may be obtained by isolation from dried leaves of *Salvia divinorum*. As an example, leaves may be thoroughly dried and finely powdered. The powdered leaves were percolated thrice with acetone at room temperature. The extract is dried, redissolved in boiling ethanol, allowed to stand for the first 24 hours at room temperature and then moved to a refrigerator for another 48 hours. Salvinorin A is harvested from the cold ethanol by vacuum filtration. Two recrystallizations yield analytically pure salvinorin A. The structure of salvinorin A may be confirmed by comparison with an authentic sample and analysis of its NMR and mass spectra.

Chemical Modifications of Salvinorin A

Purely by way of example of the present invention, salvinorinyl-2-thioacetate, 2-thiol salvinorin B, salvinorinylamide-2-acetamide, salvinorinylamide-2-amine are tested to show their potent affinities for KOR.

Natural Products

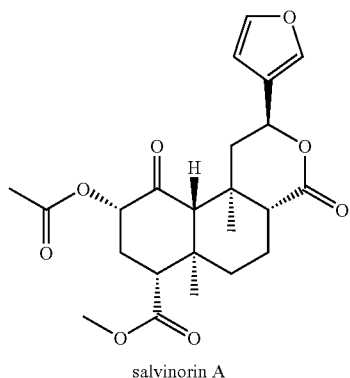
salvinorin A

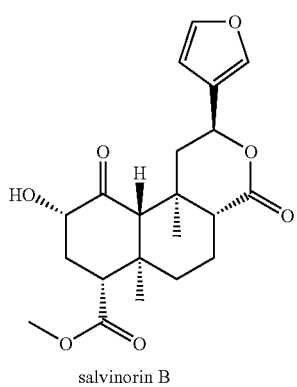
salvinorin B

Bioisosteres

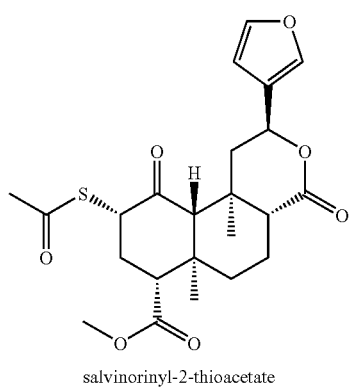
salvinorinyl-2-thioacetate

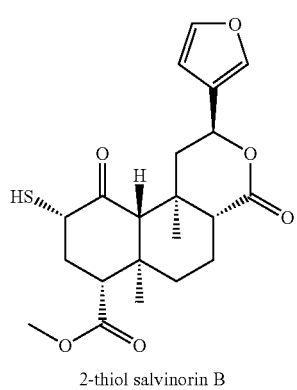
2-thiol salvinorin B

-continued salvinorinylamide-2-acetamide salvinorinylamide-2-amine

| Compounds | $K_i$ (nM) |
| --- | --- |
| Salvinorin A | 4.4 |
| Salvinorin B | >10000 |
| Salvinorinyl-2-thioacetate | 7.9 |
| 2-Thiol salvinorin B | 11.2 |
| Salvinorinylamide-2-acetamide | NT |
| Salvinorinylamide-2-amine | NT |

Sulfur- and nitrogen-derivatives are useful for in vivo occupancy of KOR's and, thus, provide for long-term activation or inactivation of KOR's in a variety of disease states. Since KOR's have been implicated in a wide variety of disease processes including: dementia, mood disorders, schizophrenia, drug abuse, alcohol addiction, chronic pain conditions, seizure disorders, cognition enhancement, congestive heart failure, renal failure, augmentation of renal function, and diuresis, long-acting agonists or antagonists of KOR's would be useful for treating a variety of disease states.

EXPERIMENTAL/EXAMPLES

The following examples are provided for exemplary purposes and are not intended to limit the present invention in any way.

Formation of Reactive Alkyl Halide Intermediates

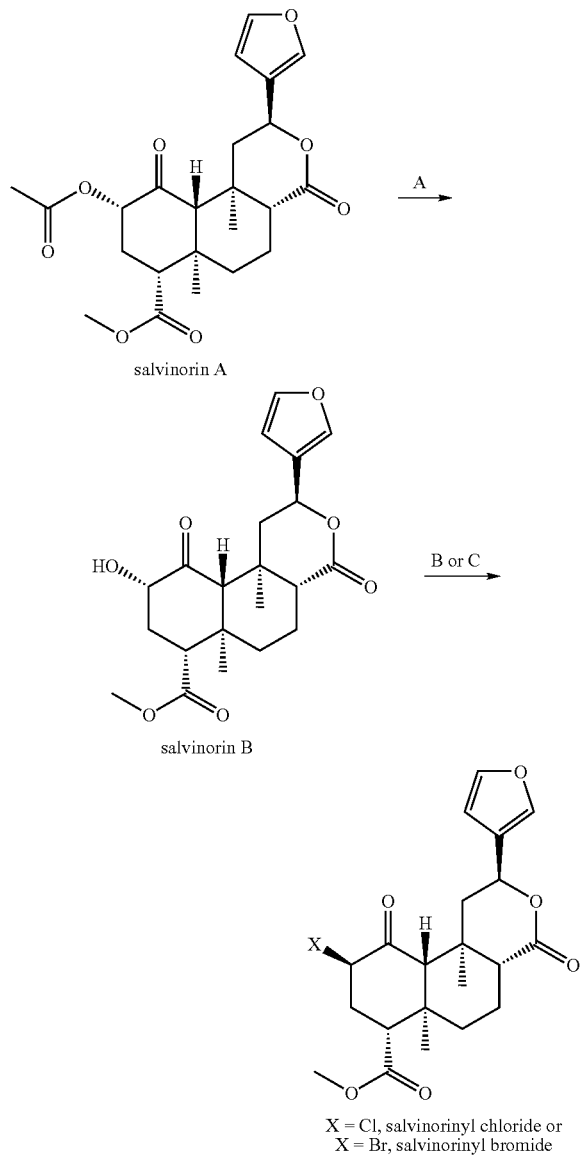

A. Salvinorin B

Salvinorin A (about 1.0 g, 2.3 mmol) is placed in methanol (about 100 mL) containing sodium or potassium bicarbonate or carbonate (about 1.0 g, excess) and stirred for two days. The solution becomes homogenous over the first day and then salvinorin B begins to precipitate. Water (about 20 mL) is added, the solution filtered, and the cake washed with cold methanol to afford analytically pure salvinorin B (about 719 mg, 2.0 mmol). The filtrate can be concentrated to remove the methanol and shaken with ethyl acetate to transfer unprecipitated salvinorin B to the organic layer. A short silica column using hexanes:ethyl acetate (1:1) as mobile phase affords additional salvinorin B (about 71 mg, 0.2 mmol). Total yield: about 790 mg (88%).

B. Salvinorinyl-2-chloride

Salvinorin B (about 1.0 g, 2.0 mmol) is placed in anhydrous $CH_2Cl_2$ (about 100 mL) with anhydrous pyridine (about 1.0 mL) and thionyl chloride (about 0.5 mL). The reaction is refluxed for several hours and the reaction allowed to reach r.t. The reaction mixture is washed twice with water (about 100 mL) then twice with about 10% aqueous HCl solution (about 100 mL). The organic layer is separated, dried over anhydrous $Na_2SO_4$, and concentrated in vacuo to give a crude product as a dark yellow oil. The product is purified through column chromatography using a short silica column and hexanes:ethyl acetate (about 1:1). The pure product, salvinorinyl-2-chloride, is a yellow powder. Total yield: about 300 mg (29%).

C. Salvinorinyl-2-bromide

Salvinorin B (about 200 mg, 513 µmol) is placed in anhydrous $CH_2Cl_2$ (about 15 mL) with anhydrous pyridine (about 200 µL) and thionyl bromide (about 50 µL). The reaction refluxed for 5 hours and the reaction allowed to reach r.t. The reaction mixture is washed twice with water (about 15 mL) then twice with 10% aqueous HCl solution (about 15 mL). The organic layer is separated, dried over anhydrous $Na_2SO_4$, and concentrated in vacuo to give a crude product as yellow oil. The product is purified through column chromatography using a short silica column and hexanes:ethyl acetate (1:1). The pure product, salvinorinyl-2-bromide, is a white powder. Total yield: about 138 mg (61%).

Formation of Thio-Derivatives

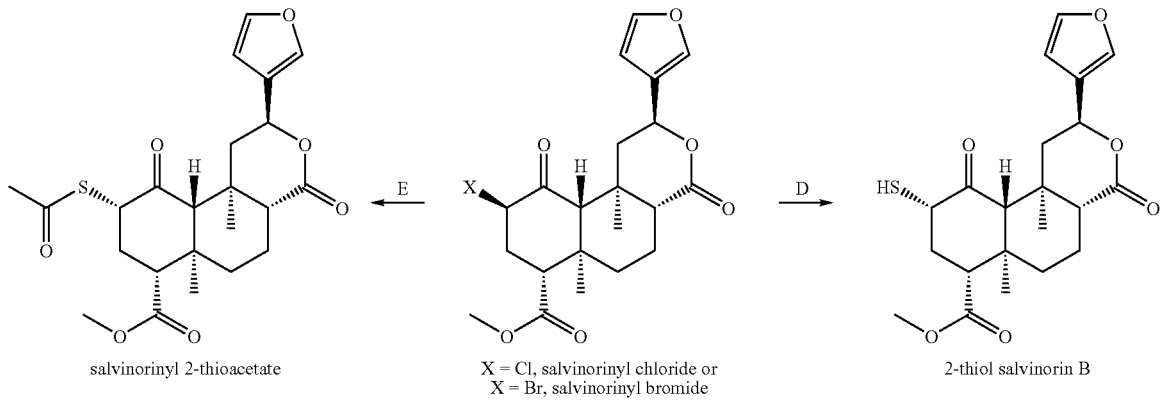

D. 2-Thiol Salvinorin B

Salvinorinyl-2-chloride (about 15.7 mg, 39 μmol) is placed in DMF (about 2 mL) containing sodium hydrogen sulfide (about 6.4 mg, 115 μmol), and the mixture heated to 35-40° C. for 1 hour. Brine water (about 2 mL) and ethyl acetate were added, the mixture shaken, and the organic layer removed. After 3 extractions, the organic layer is concentrated in vacuo, redissolved in acetone (HPLC grade, about 1 mL), and separated by HPLC ($C_{18}$ column, ACN:$H_2O$ about 1:1, detection 210 nm). 2-Thiol salvinorin B resolved at $R_t$=about 8.9 min. Total yield: about 6.9 mg (44%).

Salvinorinyl-2-bromide (about 16.6 mg, 38 μmol) is placed in DMF (about 2 mL) containing sodium hydrogen sulfide (about 6.4 mg, 115 μmol), and the mixture heated to about 35-40° C. for 1 hour. Brine water (about 2 mL) and ethyl acetate were added, the mixture shaken, and the organic layer removed. After 3 extractions, the organic layer is concentrated in vacuo, redissolved in acetone (HPLC grade, 1 mL), and separated by HPLC ($C_{18}$ column, ACN:$H_2O$ 1:1, detection 210 nm). 2-Thiol salvinorin B resolved at $R_t$=about 8.9 min. Total yield: about 6.9 mg (44%).

E. Salvinorinyl-2-thioacetate

Salvinorinyl-2-chloride (about 30.0 mg, 74 μmol) is placed in acetone (about 10 mL) containing potassium thioacetate (about 30 mg, 263 μmol) and the mixture refluxed for 3 hours. The reaction is allowed to cool to r.t., concentrated in vacuo, redissolved in acetone (HPLC grade, 1 mL), and separated by HPLC ($C_{18}$ column, $CH_3CN$:$H_2O$ (1:1), detection 210 nm). Salvinorinyl-2-thioacetate resolved at $R_t$=11.2 min. Total yield: about 22 mg (66%).

Salvinorinyl-2-bromide (about 32.8 mg, 74 μmol) is placed in acetone (10 mL) containing potassium thioacetate (about 30 mg, 263 μmol) and the mixture refluxed for 3 hours. The reaction is allowed to cool to r.t., concentrated in vacuo, redissolved in acetone (HPLC grade, 1 mL), and separated by HPLC ($C_{18}$ column, $CH_3CN$:$H_2O$ (1:1), detection 210 nm). Salvinorinyl-2-thioacetate resolved at $R_t$=about 11.2 min. Total yield: about 22 mg (66%).

Formation of Amino-Derivatives

F. Salvinorinylamide-2-amine

Salvinorinyl-2-bromide (about 94.0 mg, 214 μmol) is placed in a pressure vessel with liquid ammonia at r.t. for about 12 hours. After allowing the ammonia to evaporate, the reaction is partitioned between water and ethyl acetate. The organic layer is dried over sodium sulfate, evaporated in vacuo, and separated by silica column chromatography to yield salvinorinylamide-2-amine as an off-white powder. Total yield: about 11.1 mg (14%).

G. Salvinorinylamide-2-amine

Salvinorinylamide-2-amine (about 4.0 mg, 10 μmol) is placed in acetic anhydride (5 mL) containing anhydrous pyridine (about 100 μL) and the mixture refluxed for about 1 hour. After removal from the heat and reaching r.t., the reaction is partitioned between water and ethyl acetate. The organic layer is separated and washed thrice with saturated sodium bicarbonate. The organic layer is dried over sodium sulfate and purified by silica column chromatography to yield salvinorinylamide-2-acetamide. Total yield: about 2.4 mg (56%).

Preparation of Radiolabeled Reagents, $H_2^{35}S$ and $^{35}S$-Thioacetic Acid The available forms of $^{35}S$-labeled compounds are sodium sulfate and sulfuric acid. Sulfuric acid can be reduced to give $H_2S$, or in this case, $H_2^{35}S$. To avoid isotopic dilution of $^{35}S$ $H_2SO_4$ by the traces of sulfates present in the reducing mixture HI/HCl/$H_3PO_2$, the mixture is pretreated by heating at 110° C. for 1 hr.[6]

$H_2^{35}S$: (Boullais et al 1997)

A mixture of $H_2O$/HCl/HI/$H_3PO_2$: about 5.3/4.7/10/2.5 v/v (5 mL) is introduced in a vessel and heated at about 110° C. for about 45 min while bubbling helium (about 0.9 L/hr) then cooled at room temperature. To the pretreated reducing mixture, $^{35}S$—$H_2SO_4$ (400mCi-14.8 Tbq, SA=1243 mCi/mmol-46 Tbq/mmol, about 200 μL) is added and heated at about 110° C. for about 45 mm while bubbling helium (about 0.4 L/hr). $^{35}S$—$H_2S$ can saturate a cooled solution of sodium hydroxide to form $^{35}S$-labeled sodium hydrogen sulfide.

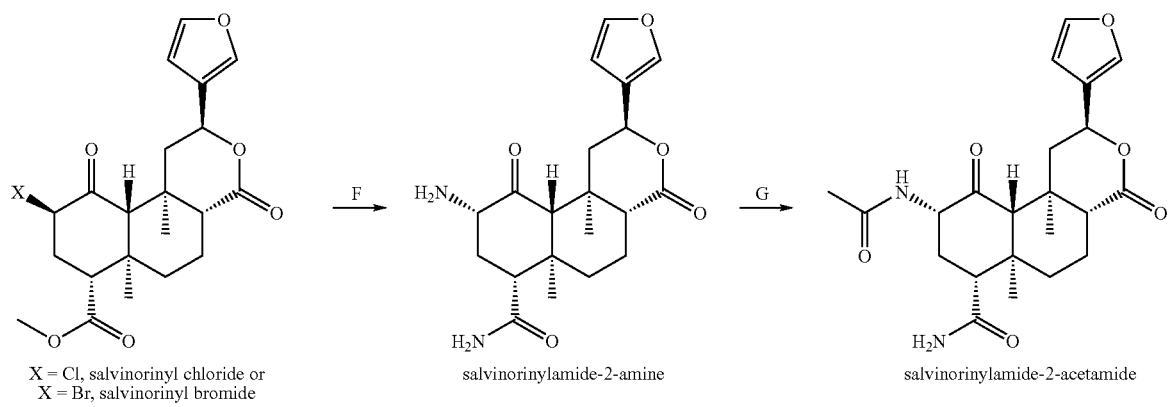

X = Cl, salvinorinyl chloride or
X = Br, salvinorinyl bromide salvinorinylamide-2-amine salvinorinylamide-2-acetamide ³H, ¹⁴C, and/or ³⁵S-Thioacetic Acid (Egli et al 1987)

Acetic anhydride can be purchased as either cold, ³H-labeled at the methyl, singly ¹⁴C-labeled at either carbon, or doubly ¹⁴C-labeled at both carbons.

Acetic anhydride (about 50 mmol), sodium hydroxide powder (about 1.1 mmol), and a stirring bar were placed into a 25 mL flask. The flask is connected to a bridge on a vacuum line, cooled, and evacuated. The stirred mixture is heated at about 55° C., and $H_2^{35}S$ (10 mmol, 200 mCi) is added, in portions, at slightly below atmospheric pressure; most of the $H_2^{35}S$ is absorbed after 2 hr. $H_2S$ is then added during 8 hr (total uptake about 38 mmol), until the rate of the reaction had become very slow, and the mixture is distilled on a vacuum line to eliminate sodium salts. ³⁵S-labeled thioacetic acid is distilled at 760 torr (about 90-93° C.) by means of a 12 in. Vigreux column to yield 2.7 g (about 35 mmol; 112 mCi). ³⁵S-labeled thioacetic acid can then be titrated with an aqueous solution of KOH to yield ³⁵S-labeled potassium thioacetate.

Preparation of Radiolabeled Sulfur-Derivatives

H. ³⁵S-2-Thiol Salvinorin B

Salvinorinyl-2-chloride (about 15.7 mg, 38 μmol) is placed in DMF (about 2 mL) containing ³⁵S-sodium hydrogen sulfide (about 6.4 mg, 115 μmol), and the mixture heated to about 35-40° C. for 1 hour. Brine water (about 2 mL) and ethyl acetate were added, the mixture shaken, and the organic layer removed. After 3 extractions, the organic layer is concentrated in vacuo, redissolved in acetone (HPLC grade, 1 mL), and separated by HPLC ($C_{18}$ column, $CH_3CN:H_2O$ 1:1, detection 210 nm). ³⁵S-2-Thiol salvinorin B resolved at $R_t$=8.9 min. Total yield: 6.9 mg (44%).

Salvinorinyl-2-bromide (about 16.6 mg, 38 μmol) is placed in DMF (2 mL) containing ³⁵S-sodium hydrogen sulfide (about 6.4 mg, 115 μmol), and the mixture heated to about 35-40° C. for 1 hour. Brine water (about 2 mL) and ethyl acetate were added, the mixture shaken, and the organic layer removed. After 3 extractions, the organic layer is concentrated in vacuo, redissolved in acetone (HPLC grade, 1 mL), and separated by HPLC ($C_{18}$ column, $CH_3CN:H_2O$ 1:1, detection 210 nm). ³⁵S-2-Thiol salvinorin B resolved at $R_t$=8.9 min. Total yield: about 6.9 mg (44%).

I. ³⁵S-Salvinorinyl-2-thioacetate

Salvinorinyl-2-chloride (about 30.0 mg, 74 μmol) is placed in acetone (10 mL) containing ³⁵S-potassium thioacetate (about 30 mg, 263 μmol) and the mixture refluxed for about 3 hours. The reaction is allowed to cool to r.t., concentrated in vacuo, redissolved in acetone (HPLC grade, 1 mL), and separated by HPLC ($C_{18}$ column, $CH_3CN:H_2O$ (1:1), detection 210 nm). Salvinorinyl-2-thioacetate resolved at $R_t$=11.2 min. Total yield: about 22 mg (66%).

Salvinorinyl-2-bromide (about 32.8 mg, 74 μmol) is placed in acetone (10 mL) containing ³⁵S-potassium thioacetate (about 30 mg, 263 μmol) and the mixture refluxed for 3 hours. The reaction is allowed to cool to r.t., concentrated in vacuo, redissolved in acetone (HPLC grade, 1 mL), and separated by HPLC ($C_{18}$ column, $CH_3CN:H_2O$ (1:1), detection 210 nm). Salvinorinyl-2-thioacetate resolved at $R_t$=11.2 min. Total yield: about 22 mg (66%).

Preparation of Radiolabeled Nitrogen-Derivatives

J. ¹⁵N-Salvinorinylamide-2-amine

Salvinorinyl-2-bromide (about 94.0 mg, 214 μmol) is placed in a pressure vessel with liquid ¹⁵N-ammonia at r.t. for 12 hours. After allowing the ammonia to evaporate, the reaction is partitioned between water and ethyl acetate. The organic layer is dried over sodium sulfate, evaporated in vacuo, and separated by silica column chromatography to yield salvinorinylamide-2-amine as an off-white powder. Total yield: about 11.1 mg (14%).

K. ¹⁵N-Salvinorinylamide-2-amine

¹⁵N-Salvinorinylamide-2-amine (about 4.0 mg, 10 μmol) is placed in *acetic anhydride (about 5 mL) containing anhydrous pyridine (about 100 μL) and the mixture refluxed for 1 hour. After removal from the heat and reaching r.t., the reaction is partitioned between water and ethyl acetate. The organic layer is separated and washed thrice with saturated sodium bicarbonate. The organic layer is dried over sodium sulfate and purified by silica column chromatography to yield ¹⁵N-salvinorinylamide-2-acetamide. Total yield: about 2.4 mg (56%).

*Acetic anhydride can be purchased as either cold, ³H-labeled at the methyl, singly ¹⁴C-labeled at either carbon, or doubly ¹⁴C-labeled at both carbons.

LITERATURE CITED

The following references are incorporated herein by reference:

Boullais, C.; Riva, M.; Noel, J. P. New chemo-enzymatic synthesis of very high specific radioactivity [35S] (S) methionine [1]. *J Label. Cmpds. Radiopharm.* 1997, 39, 621-624.

Butelman, E. R.; Harris, T. J.; Kreek, M. J. The plant-derived hallucinogen, salvinorin A produces κ-opioid agonist-like discriminative effects in rhesus monkeys. *Psychopharm.* 2004, 172, 220-224.

Chao, C. C.; Gekker, G.; Hu, S.; Kravitz, F.; Peterson, P. K. Kappa-opioid potentiation of tumor necrosis factor-alpha-induced anti-HIV-1 activity in acutely infected human brain cell cultures. *Biochem. Pharmacol.* 1998, 56, 397-404.

Chavkin, C.; Sud, S.; Wenzhen, J.; Stewart, D. J.; Zjawiony, J. K.; Renock, S.; Baner, K.; White, N. M.; Pintar, J.; Roth, B. L. Salvinorin A, an active component of the hallucinogenic sage *Salvia divinorum* is a Highly Efficacious Kappa Opioid Receptor Agonist: Structural and functional considerations. *J. Pharm. Exp. Ther.* 2004, 308, 1197-1203.

Egli, P. and Migdalof, B. H. Synthesis of labeled captopril. *J. Label. Cmpds. Radiopharm.* 1987, 25, 1105-1115.

Ortega, A.; Blount, J. F.; Manchand, P. S. Salvinorin, a new trans-neoclerodane diterpene from *Salvia divinorum* (Labiatae), *J. Chem. Soc., Perkin Trans.* 1, 1982, 10, 2505-2508.

Roth, B. L.; Baner, K.; Westkaemper, R.; Siebert, D.; Rice, K. C.; Steinberg, S.; Ernsberger, P.; Rothman, R. B. Salvinorin A: A potent, naturally occuring, non-nitrogenous κ-opioid selective agonist, *PNAS*, 2002, 99(10), 11934-11939.

Siebert, D. J., *Salvia divinorum* and salvinorin A: New pharmacological findings. *J. Ethnopharmacol.* 1994, 43, 53-56.

Valdes III, L. J.; Butler, W. M.; Hatfield, G. M.; Paul, A. G.; Koreeda, M. Divinorin A, a psychotropic terpenoid, and divinorin B from the hallucinogenic Mexican mint *Salvia divinorum*. *J. Org. Chem.* 1984, 49, 4716-4720.

The invention thus being described, it will be obvious that the same can be varied in many ways. All such variations are considered to be within the scope of the invention and not a departure therefrom.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this disclosure, various publications are referenced. All such references are incorporated herein by reference.

We claim:

1. A compound of the following general formula, which includes salts thereof:

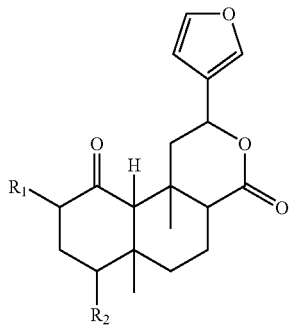

wherein:
R$_1$ and/or R$_2$ is hydrogen, halogen, alkyl, hydroxyl, alkoxyl, acyloxyl, hydroxyalkyl, amino, alkylamino, acylamino, acetylalkylamino, arylamino, arylalkylamino, Het-alkylamino, aminoalkyl, acylaminoalkyl, nitroalkyl, thiol, alkylthio, acylthio, arylthio, arylalkylthio, acetylalkylthio, carboxylic acid ester, amide, —CONH$_2$, and nitrile derivatives thereof, provided that R$_1$ is not

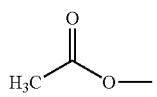

when R$_2$ is

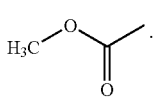

2. A compound of claim 1, further comprising at least one isotopic label.

3. A compound of claim 2, wherein radioisotopes of at least one of hydrogen, carbon, oxygen, sulfur- or nitrogen atoms are present.

4. A compound of claim 1, of the following formula:

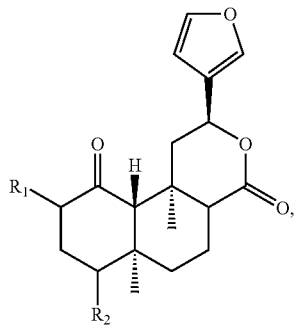

wherein R$_1$ and/or R$_2$ is hydrogen, halogen, alkyl, hydroxyl, alkoxyl, acyloxyl, hydroxyalkyl, amino, alkylamino, acylamino, acetylalkylamino, arylamino, arylalkylamino, Het-alkylamino, aminoalkyl, acylaminoalkyl, nitroalkyl, thiol, alkylthio, acylthio, arylthio, arylalkylthio, acetylalkylthio, carboxylic acid ester, amide, —CONH$_2$, and nitrile derivatives thereof, provided that R$_1$ is not

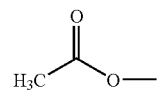

when R$_2$ is

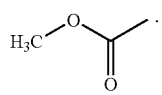

5. A compound of claim 4, further comprising at least one isotopic label.

6. A compound of formula 1 of the following formula:

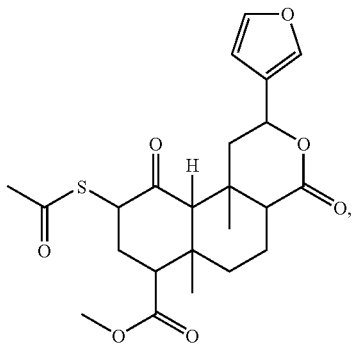

salvinorinyl-2-thioacetate and salts thereof.

7. A compound of claim 6, further comprising at least one isotopic label.

8. A compound of formula 1 of the following formula:

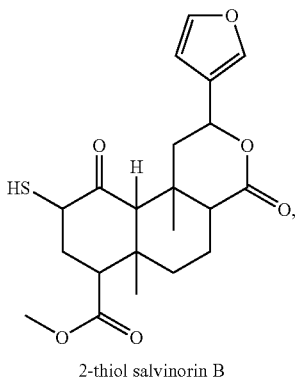

2-thiol salvinorin B and salts thereof.

9. A compound of claim 8, further comprising at least one isotopic label.

10. A compound of formula 1 of the following formula:

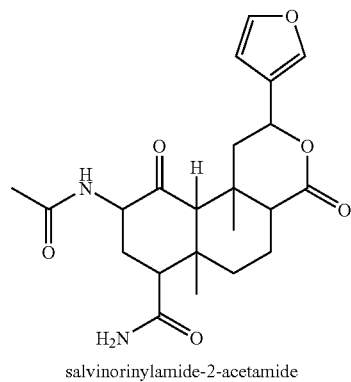

salvinorinylamide-2-acetamide and salts thereof.

11. A compound of claim 10, further comprising at least one isotopic label.

12. A compound of formula 1, of the following formula:

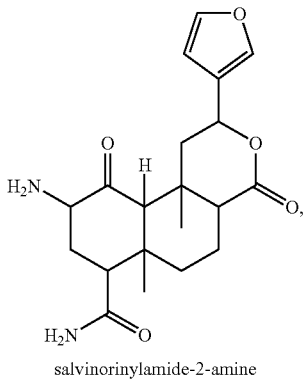

salvinorinylamide-2-amine and salts thereof.

13. A compound of claim 12, further comprising at least one isotopic label.

14. A composition comprising a compound of a claim 1, or a salts thereof and a pharmaceutically acceptable carrier.

15. A composition of claim 14, further comprising an isotopic label.

16. A method of detecting or monitoring KOR activity, comprising: providing a compound of the following formula:

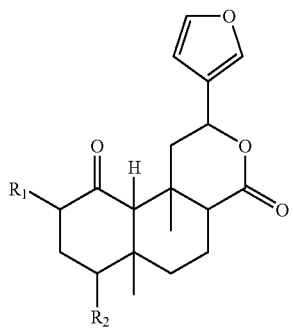

wherein:

$R_1$ and/or $R_2$ is hydrogen, halogen, alkyl, hydroxyl, alkoxyl, acyloxyl, hydroxyalkyl, amino, alkylamino, acylamino, acetylalkylamino, arylamino, arylalkylamino, Het-alkylamino, aminoalkyl, acylaminoalkyl, nitroalkyl, thiol, alkylthio, acylthio, arylthio, arylalkylthio, acetylalkylthio, carboxylic acid, —$CONH_2$, derivatives thereof (such as esters, amides, and nitriles);

or pharmaceutically acceptable salts thereof provided that the compound has an isotopic label;

introducing said composition to a subject; and detecting the binding of the compound to KOR.

17. The method of claim 16, wherein the detecting step is in vivo or in vitro.

18. The method of claim 16, wherein the subject is a human.

19. The method of claim 16, wherein the compound is detected by at least one of PET, SPECT, and/or NMR imaging.

20. The method of claim 16, further comprising correlating binding of the compound to KOR with a disease state or condition.

21. The method of claim 16, further comprising correlating binding of the compound to KOR with the presence of a KOR-expressing tumor.

* * * * *